United States Patent
Wellinghoff et al.

(10) Patent No.: US 6,696,585 B1
(45) Date of Patent: *Feb. 24, 2004

(54) FUNCTIONALIZED NANOPARTICLES

(75) Inventors: Stephen T. Wellinghoff, San Antonio, TX (US); Hong Dixon, Helotes, TX (US); Henry R. Rawls, San Antonio, TX (US); Barry K. Norling, San Antonio, TX (US)

(73) Assignees: Southwest Research Institute, San Antonio, TX (US); Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/667,370

(22) Filed: Sep. 22, 2000

Related U.S. Application Data

(62) Division of application No. 09/103,197, filed on Jun. 23, 1998, now Pat. No. 6,258,974, which is a continuation-in-part of application No. 08/721,742, filed on Sep. 27, 1996, now abandoned, which is a continuation-in-part of application No. 08/298,836, filed on Aug. 31, 1994, now Pat. No. 5,670,583, which is a division of application No. 08/047,750, filed on Apr. 13, 1993, now Pat. No. 5,372,796.

(51) Int. Cl.$^7$ .............................. C07F 9/08; C07F 7/02
(52) U.S. Cl. ............... 556/10; 252/299.64; 252/299.01; 552/309; 556/12; 560/61; 560/67; 560/70; 525/360; 525/361; 525/389; 523/212; 523/213
(58) Field of Search .................... 560/61, 67, 70; 556/10, 12; 252/299.01, 299.64; 552/309; 525/360, 361, 389; 523/212, 213

(56) References Cited

U.S. PATENT DOCUMENTS

| | | |
|---|---|---|
| 4,215,033 A | 7/1980 | Bowen |
| 4,299,943 A * | 11/1981 | DiGiacomo et al. ........... 528/9 |
| RE32,073 E | 1/1986 | Randklev |
| 4,588,756 A | 5/1986 | Bowen |
| 4,623,738 A | 11/1986 | Sugerman et al. |
| 4,659,751 A | 4/1987 | Bowen |
| 4,964,911 A | 10/1990 | Ibsen |
| 4,978,640 A | 12/1990 | Kelly |
| 5,030,608 A | 7/1991 | Schubert et al. |
| 5,057,018 A | 10/1991 | Bowen |
| 5,064,877 A | 11/1991 | Nass et al. |
| 5,073,294 A | 12/1991 | Shannon et al. |
| 5,202,053 A | 4/1993 | Shannon et al. |
| 5,276,068 A | 1/1994 | Waknine |
| 5,308,886 A | 5/1994 | Masuhara et al. |
| 5,328,947 A | 7/1994 | Taguchi et al. |
| 5,334,625 A | 8/1994 | Ibsen et al. |
| 5,372,796 A | 12/1994 | Wellinghoff |
| 5,401,528 A | 3/1995 | Schmidt |
| 5,472,797 A | 12/1995 | Yajima et al. |
| 5,486,548 A | 1/1996 | Podszun et al. |
| 5,502,087 A | 3/1996 | Tateosian et al. |
| 5,556,931 A | 9/1996 | Imura et al. |
| 5,563,230 A | 10/1996 | Hsu et al. |
| 5,654,471 A | 8/1997 | Zahn et al. |
| 5,663,214 A | 9/1997 | Okada |
| 5,670,583 A | 9/1997 | Wellinghoff |
| 5,730,601 A | 3/1998 | Bowman et al. |
| 5,833,880 A | 11/1998 | Siemensmeyer |
| 5,834,532 A | 11/1998 | Yamamoto et al. |
| 5,852,248 A | 12/1998 | Chadwick |
| 5,859,089 A | 1/1999 | Qian |
| 5,865,623 A | 2/1999 | Suh |
| 5,886,064 A | 3/1999 | Rheinberger et al. |
| 5,897,885 A | 4/1999 | Petticrew |
| 5,910,273 A | 6/1999 | Thiel et al. |
| 5,955,514 A | 9/1999 | Huang et al. |
| 5,989,461 A | 11/1999 | Coates et al. |
| 5,998,499 A | 12/1999 | Klee et al. |
| 6,027,816 A | 2/2000 | Ono et al. |
| 6,031,015 A | 2/2000 | Ritter et al. |
| 6,090,308 A | 7/2000 | Coates et al. |
| 6,417,244 B1 * | 7/2002 | Wellinghoff et al. ........ 522/104 |

FOREIGN PATENT DOCUMENTS

| | | |
|---|---|---|
| CA | 2181507 | 7/1996 |
| EP | 0 159 877 A1 | 10/1985 |
| EP | 0159 887 A2 | 10/1985 |
| EP | 0 754 675 A2 | 1/1997 |
| JP | H 3-344860 | 12/1991 |
| WO | WO 92/16183 | 10/1992 |
| WO | WO 93/22397 | 11/1993 |
| WO | WO 94/24052 | 10/1994 |
| WO | WO 97/14674 | 4/1997 |
| WO | WO 98/13008 | 4/1998 |

OTHER PUBLICATIONS

"Nanostructured Materials: A Technical–Market Analysis", Mindy N. Rittner, Business Communications Co., Inc.; Fine, Ultrafine and Nano Powders, 1998.

Y. Wei, et al., "Synthesis of New Organic–Inorganic Hybrid Glasses"; Chem. Mater. 2(4), 337 (1990).

(List continued on next page.)

Primary Examiner—Shailendra Kumar
(74) Attorney, Agent, or Firm—Paula D. Morris & Associates, P.C.

(57) ABSTRACT

There are disclosed amphoteric nano-sized metal oxide particles functionalized with silyl esters of a phosphonate and composites thereof with an acrylate-based monomer, including liquid crystal monomers photopolymerizable at ambient temperature. Also disclosed are the method making such functionalized particular by reacting a metal oxide with a silyl ester of a phosphonate in the presence of a non-aqueous solvent and in an inert atmosphere and the method of making the composites wherein the functionalized particles are admixed with an acrylate-based matrix monomer, including liquid crystal monomers photopolymerizable at ambient temperature. Further disclosed is the method of dental repair wherein the composites are applied to a tooth and photopolymerized.

21 Claims, No Drawings

OTHER PUBLICATIONS

Steven T. Wellinghoff and Scott F. Timmons, Sol–Gel Processign and Application, Edited by Y.A. Attia, "Tantalum Oxide–Polymer Composites", Plemnum Press, New York, 1994, pp. 141–154.

H. Schmidt & H. Wolter, J. of Non. Cryst. Solids, 121. 428–435 (1990).

C.J.T. Landry, et al., Polymer, 33 (7), 1487 (1992).

M. Ellsworth et al. JACS, 113(7), 2756 (1991).

Michael J.S. Dewar, et al., "Factors Influencing the Stabilities of Nematic Liquid Crystals", Jornal of American Chemical Society, 97:23, 6658–6666, 1975.

Wolfgang Wedler, et al., "Vitrification in Low–molecular–weight mesogenic Compounds", J. Mater. Chem., 1991, 1(3), 347–356.

Sukmin Lee, et al., "Phase Behavior of Liquid Crystalline Polymer/Model Compound Mixtures: Theory and Equipment", Macromolecules, vol. 27, No 14, 1994, 3955–3962.

R.A.M. Hikmet, et al., "Effect of the Orientation of the Ester Bonds on the Properties of Three Isomeric Liquid Crystal Diacrylates Before and After Polymerization", Macromolecules, vol. 28, No. 9, 1995, 3313–3327.

* cited by examiner

FUNCTIONALIZED NANOPARTICLES

CROSS-REFERENCES TO RELATED APPLICATIONS

The instant application is a divisional application Ser. No. 09/103,197, filed Jun. 23, 1998, now U.S. Pat. No. 6,258,974 which is a Continuation-in-Part of U.S. application Ser. No. 08/721,742, filed Sep. 27, 1996, now abandoned, which is a Continuation-in-Part of U.S. application Ser. No. 08/298,836, filed Aug. 31, 1994, now U.S. Pat. No. 5,670,583, which is a Division of U.S. application Ser. No. 08/047,750, filed Apr. 13, 1993, now U.S. Pat. No. 5,372,796. The entirety of the specifications and claims of the foregoing applications are specifically incorporated herein by reference.

The U.S. government has certain rights in this invention pursuant to grant number NIDCR 1 P01 DE11688.

BACKGROUND OF THE INVENTION

The instant invention relates to alkene functionalized, metal oxide, nanoparticle composites with polymerizable alkene matrix monomers primarily suitable for dental and medical restoration; i.e., dental restoratives and bone repair, and to the method of their use for such purposes and methods of manufacture. Other applications envisioned include optical elements, X-ray photoresists, and repair of materials.

There have been efforts made to generate functionalized metal oxide nanoparticles to make highly uniform composite materials; namely, in U.S. Pat. No. 5,064,877 by R. Nass et al., in U.S. Pat. No. 5,030,608 by U. Schubert et al. (see also H. Schmidt and H. Wolter, J. Non. Cryst. Solids, 121, 428 (1990). They claim a method for producing functionalized, photopolymerizable particles by replacing groups, R, in $M(R)_n$ with groups A which complex M and further contain functional groups which can be photopolymerized. The dispersed, individual metal oxide particles can be prepared by removing R completely, partially replacing by A and then by hydrolyzing to oxide with water. Alternatively, the oxyhydroxide particles may be preformed as $M(O)_z(OH)_xR_y$ and converted to $M(O)_z(OH)_xA_y$ by the loss of R. The preformed oxyhydroxide is formed by Nass et al. by the hydrolysis of the organometallic $M(R)_n$ by water directly or by water generated by reaction of acid and alcohol unlike Wellinghoff in U.S. Pat. No. 5,570,583 where the oxide is formed by direct ester exchange between a metal alkoxide and a strong organic acid thereby decreasing the number of required reactants.

There have been other attempts to form organic-inorganic hybrid glasses. However, in one case a silane functionalized polymer is hydrolyzed with water to form a network crosslinked by the resultant silica particles making removal of volatile reaction products difficult [Y. Wei et al., Chem. Mater., 2(4), 337 (1990); C. J. T. Landry et al., Polymer, 33(7), 1487 (1992)]. M. Ellsworth et al. [JACS, 113(7), 2756 (1991); U.S. Pat. Nos. 5,412,043; 5,254,638] attempted to eliminate the composite shrinkage induced by removal of volatile reaction products by utilizing ring strained alkenoxysilanes and polymerizable solvents where all reaction by products contribute to the $SiO_2$ network or the resultant interpenetrating, matrix, organic polymer. The expected packing disruption induced by the strained ring opening of the alkenoxysilane was a strategy for compensating for the shrinkage induced by conversion of double bonds to single bonds Zero polymerization shrinkage is one of the most necessary features of a dental restorative so that accumulated stresses do not debond the dentin-restorative interface or fracture the tooth or restorative which can result marginal leakage and microbial attack. This feature is also important in bone repair and in accurate reproduction of photolithographic imprints and optical elements.

Other attempts have been made to reduce polymerization shrinkage by utilizing nematic liquid crystal monomers. The expected low polymerization shrinkage for such compounds originates from the high packing efficiency that already exists in the nematic state, thus minimizing the entropy reduction that occurs during polymerization. Liquid crystal monomers or prepolymers have another advantage in that the viscosity is lower than an isotropic material of the same molecular weight.

M. Aizawa et al. [JP H 5-178794, Jul. 30, 1993] disclose a bisalkene substituted liquid crystal crystal monomer that is suitable for dental restorative materials in combination with silica particle reinforcement. Latter H. Ritter [EP 0,754,675 A2] et al. also disclose liquid crystal monomers that might be suitable for dental applications; however, in neither of the above two patents was the liquid crystal nematic at room temperature or dental temperature. Reactive diluents were added to the original compounds to generate liquid monomers and it was not clear that liquid crystallinity was present in these mixtures. However, even more recently, J. Klee et al. [WO 97/14674] discuss two liquid crystal monomers that are nematic in the desired temperature range between room temperature and 37° C.

Parent U.S. application Ser. No. 08/721,742, identified above, discloses bisalkene terminated liquid crystal monomers that form stable liquid crystalline melts between room temperature and 37° C. and their composites with functionalized nanoparticles. This disclosure describes the nanoparticles formed by the reaction of trialkylchlorosilane, formic acid and tantalum alkoxide that are quite acidic in concentrated methanol solution and must be surface functionalized with the base, vinyl imidazole in order to neutralize the excess acidity. The alternative functionalization with an alkene phosphate suffers from the relative hydrolytic instability of the phosphate linkage and the low selectivity of the alkene dimethyl phosphate ester for reaction with Ta—OH bonds. While very satisfactory, the composites are, however, hydrophilic, and this mitigates against their complete suitability for dental purposes.

SUMMARY OF THE INVENTION

The forgoing problems and deficiencies of the prior art are overcome by the instant invention which provides workable oxide-monomer mixtures with especially low polymerization shrinkage in the matrix resin while permitting high loading of strengthening materials and high matrix molecular weight, and yet permitting the matrix to strain soften, and flow onto/and or into areas to be cemented, coated, or restored, such as bone and tooth crevices, and to be polymerized between −40° C. and +40° C.

Briefly, the present invention comprises novel functionalized amphoteric nano-sized metal oxide particles, composites thereof, and transparent or translucent acrylate or methacrylate based matrix-metal oxide compositions with photopolymerizable room temperature nematics that have high strength and hardness with essentially zero shrinkage.

The invention also comprises the methods of making the composites and compositions as hereinafter set forth.

DETAILED DESCRIPTION

While the present invention can be carried out using any metal capable of forming amphoteric metal oxides to form the metal oxide nanoparticles, such as tantalum, niobium, indium, tin, titanium and the like, it will be described in connection with tantalum. Tantalum is particularly desired for dental and medical uses since it will provide X-ray opaque materials necessary for diagnosis by dental and medical personnel.

These tantalum nanoparticles are prepared as set forth in the parent application identified above by ester exchange of tantalum oxide with an acid such as formic acid.

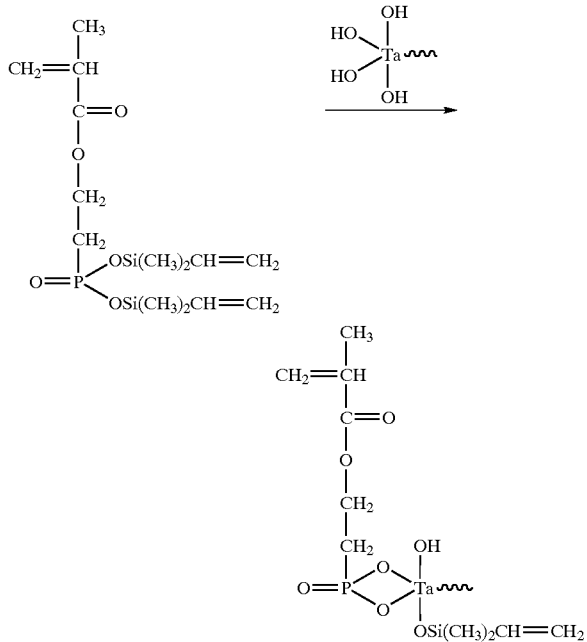

For this invention it is important that such nanoparticles be non-interacting without high surface acidity which is detrimental for dental applications, especially. In addition, it is preferable that the alkene be reacted with the oxide surface through a phosphonate linkage which has good hydrolytic stability and will react with Ta—OH bonds only through the ester bonds. In order to make an especially active phosphonating species we reacted the dimethyl ester of the methacryl phosphonate with a silanating agent to form the hydrolytically unstable vinyl dimethyl silyl ester. The silanating agent can be a chloride, as shown below, or a bromide.

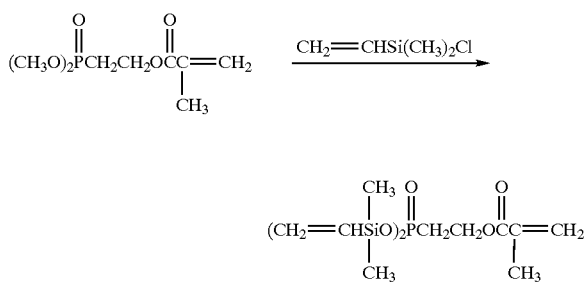

This reaction is quite generic and can be utilized to form the any trialkylsilyl ester (for example, trimethylsilyl) of any functionalized phosphonate, including vinyl phosphonate. Suitable esters have the general formula:

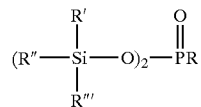

wherein R is a photopolymerizable group, such as a vinyl, acryl, or methacryl group, and R', R", and R''', which can be the same or different, are an alkyl or alkene group.

For purposes of further illustration, in addition to the trialkylsilyl ester of vinyl phosphonate, phosphonates having the following groups can also be used:

1. R is —CH=$CH_2$ and R', R", and R''' are each —$CH_3$;

2.

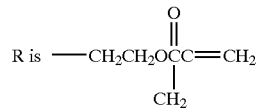

and R', R", and R''' are each —$CH_3$; and

3.

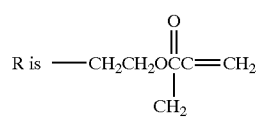

and R', R", and R''' are each —$CH_3$; and

R''' is —$CH_2$=$CH_2$

The silyl phosphonate ester can serve two purposes: one as a surface phosponating agent and the other as a surface silanating agent which will generate the hydrophobic surface necessary for incorporation into hydrophobic monomers. If the silane is alkene functionalized it will photopolymerize and immobilize into the matrix monomer, eliminating any possibility of migration out of the composite which could adversely affect the mechanical properties, such as shrinkage.

This reagent is conveniently incorporated into the preparation as set forth in the parent application identified above by ester exchange of tantalum ethoxide with an acid such as formic acid. Even though extensive phosphonating and silation of the tantalum oxyhydroxide take place the infrared spectrum still indicates a substantial amount of uncondensed Ta—OH to be present.

The remaining accessible Ta—OH can be further reduced by the addition of a trifunctional silane such as 3-(trimethoxysilyl)propyl methacrylate to the formic acid mixture. This component is also of use since the multiple Ta—O—Si bonds formed by the trifunctional silane are more hydrolytically stable than the monofunctional silanes. In addition, the silane effectively blocks access to unreacted Ta—OH bonds. Thus, interparticle hydrogen bonding associations between Ta—OH bonds on adjacent particles is blocked and premature phase separation of a tantalum rich phase in the hydrophobic matrix monomer is avoided.

Alternatively, the tantalum oxide can be prepared as in the parent application with the silyl phosphonate and trifunctional silane subsequently added to an alcohol solution of the tantalum oxide nanoparticles.

These tantalum oxide nano-sized particles, (nanoparticles) form highly acidic (pH=2–3) solutions in alcohols most probably due to absorbed acid. This is first removed by exposing the oxide solution to a crosslinked gel of poly 4-vinyl pyridine which increases the pH to 6, a value suitable for further composite manufacture. The particle size is not critical, with about 150 Å being a desirable size and over 100 Å being suitable.

A 10–30 wt % solution of tantalum oxide nanoparticles is then mixed with a solution of a matrix monomer which may be glycerol monomethacrylate, glycerol dimethacrylate, hydroxyethylmethacrylate (HEMA), 2,2-bis[p-(2'-hydroxy-3'-methacryloxypropoxy)phenylene]propane (Bis-GMA), or ethoxylated bis-GMA and various blends of these monomers in combination with known plasticizers, such as trithethyleneglycol dimethacrylate, and polypropylene oxide monomethacrylate and known photoinitiators such as camphorquinone and and photoactivators such as 2-n-butoxyethyl-4-(dimethylamino)benzoate.

After evaporation of the solvent under high vacuum at room temperature, a clear fluid mixture of the tantalum oxide and the matrix monomer is formed which can be cast into molds or coated onto substrates and photocured into a glassy transparent solid.

Composite fluids containing the more hydrophilic monomers are more stable to phase separation into a clear gel which probably contains interpenetrating tantalum rich and tantalum poor phases of such a small size scale (<3000 Å) that light scattering is minimized. Nanoparticles which are relatively more hydrophobic due to a more extensive reaction with the phosphonating or silanating reagents are also stable to phase separation in hydrophobic monomers.

For many applications which include biomedical repair, the cured composite must be resistant to swelling by saline solution at 37° C. For this reason matrix monomer blends containing high concentrations of hydrophobic monomers like ethoxylated bis-GMA are to be preferred over those containing hydrophilic monomers such as HEMA. Surface swelling by saline results in surface solvent crazing which can be deleterious to the physical strength of the composite.

Parent application Ser. No. 08/721,742 noted above describes the use of bis acrylate and methacrylate terminated liquid crystals which are especially useful as matrix monomers. Of special interest are bis-(4-(6-acrylolyloxyhexyl-1-oxy)benzoyl)2-(t-butyl)quinone (C6(H, TB,H) and bis-(4-(10-acrylolyloxydecyl-1-oxy)benzoyl)2-(t-butyl)quinone (C10(H,TB,H) both of which are nematic liquid crystals between room temperature and 40° C. In addition to the hexyl and decyl groups it is possible to make suitable nematic liquid crystals utilizing other oligoethylene groups such as heptyl, octyl, and nonyl groups. Although molecules of this general structure have been synthesized, practical application in low polymerization shrinkage applications was precluded because of the development of crystallinity at room temperature which effectively prevents manipulation of the material. However, the novel substitution of the central aromatic group with an especially bulky group such as t-butyl was found to suppress crystallinity at room temperature while still permitting the nematic state to exist. Both could be photopolymerized to about 2% linear polymerization shrinkage (5.9% volumetric shrinkage) at about 50% double bond conversion; this volumetric shrinkage is more than 2.6× less than typical commercial, unfilled resins. Addition of filler should be able to reduce this substantially because of the volume filling effect.

Even though C6(H,TB,H) of purities less than 95% can't crystallize from the melt, material purified to 99+% by column chromatography could be very slowly crystallized from methanol and diethyl ether to produce a solid that melted at 67° C. Once melted, however, the material would not recrystallize in the absence of solvent. The expensive column separation could be avoided by seeding the crude liquid crystal in methanol suspension at −20° C. with the column prepared crystals. The observation that the crude material can be solvent crystallized, but not melt crystallized is an important since it provides a cheaper recrystallization route to purification that might not rely on expensive column separation and, in addition, the desirable stability of the liquid crystalline state to premature crystallization and solidification at room temperature is maintained.

The purified C6(H,TB,H) underwent a combined smectic or nematic to isotropic transformation at 43° C. which is above the mouth temperature of 37° C., thus making it useful for polymerization out of the liquid crystalline state. A glass transition appeared at −40° C.

C6(H,TB,H) of only 90% purity (crude), and 95% purity (semicrude), respectively, either never crystallized or crystallized even more slowly to a lower melting, partially crystalline material (melting point=60° C.). In addition the smectic to isotropic and nematic to isotropic transition temperatures diverged, now changing to $T_{s->n}=25°$ C., $T_{n->isotropic}=42°$ C. for the semicrude material and $T_{s->n}=18°$ C., $T_{n->isotropic}=40°$ C. The major impurity in this material seemed to be a hydrochlorinated derivative of C6(H,TB,H), HCl (e.g. $CH_2Cl$—$CH_2$—$C(O)$—) that was generated in the acrylolyation step and was impossible to separate by column chromatography and showed a strong tendency to cocrystallize with C6(H,TB,H). It's immediate effect was to completely inhibit the ability of the C6(H,TB,H) to melt crystallize; however, no suppression of the $T_{n->isotropic}$ was noted up to at least 14% of C6(H,TB,H),HCl. Thus a clear strategy for retarding crystallization besides including a t-butyl group on the central aromatic ring is to mix liquid crystal having different end groups but the same t-butyl substituted central aromatic structure.

The importance of the above result is that considerable amounts of soluble impurity can be added to the liquid crystalline material without changing its $T_{nematic->isotropic}$ transition temperature. Thus, a high volume fraction of tantalum oxide or silicon-tantalum oxide nanoparticles (semisoluble "impurity")can be added to the liquid crystal and the resultant composite can maintain the desirable, low viscosity flow and low polymerization shrinkage characteristics of the continuous liquid crystal matrix at room temperature up to dental use temperatures.

Highly purified C6(H,TB,H) can be codissolved with at least 30 wt % tantalum oxide nanoparticles in a variety of solvents to make clear solutions. Once the solvent is pumped off a translucent pasty fluid is generated which contains partially crystallized C6(H,TB,H) nucleated by the tantalum oxide phase. These monomer crystals can be melted at 60° C. and a clear isotropic melt can be obtained down to 42° C. at which temperature the nematic phase is formed. This thermotropic transition is fully reversible. After an extended period; however, the C6(H,TB,H) will recrystallize. The crystallization can be avoided if melts containing more than about 5% of C6(H,TB,H), HCl are employed.

The compositions are prepared by mixing functionalized metal oxide nanoparticles with a photo or thermally polymerizable matrix monomer or prepolymer. The specific non-aqueous method of producing the oxide particles permits alkene functionalized (R) phosphonates and silanes to be bound to the metal oxide through —$(M-O)_2$—$P(O)$—R, —$(M-O)_{4-x}Si(R)_x$, x=1–3 linkages. The functionalized metal oxide particle is formed when activated molecules such as silyl phosphonates [$CH_2$=$CH$—$Si(Me)_2$—$O]_2$—P (O)R or (MeO)$_{4-x}$Si(R)$_x$ condense with M—OH bonds formed during the synthesis of the metal oxide nanoparticles. The silyl phosphonate is unique in that it will not only phosphate the surface but will also generate a silanol in situ which will silanate the surface of the nanoparticle. Metal phosphonate bonds are advantageous since they are more hydrolytically stable than metal silanol bonds.

The hydrophobicity of the nanoparticle can be increased by increasing the number of functionalized M—OH bonds. The ability to alter the surface of the nanoparticle in a controlled way permits control of the working time of the unpolymerized composite and modification of the final cured microphase structure of the composite material.

For example if a hydrophobic, matrix monomer and hydrophilic nanoparticles are dissolved in a common hydrophilic, solvent evaporation of the solvent will yield an initially mobile fluid which will rapidly phase separate to form an elastic gel. Elastic properties are generated by an interpenetrating network phase of hydrophilic metal oxide nanoparticles within the hydrophobic matrix. If on the other hand hydrophobic, matrix monomer and relatively hydrophobic nanoparticles are mixed in a common solvent and the solvent is evaporated, microphase separation will proceed more slowly providing increased working or storage time in the mobile state. With increased working time the kinetic development of phase separation can be terminated at different stages by polymerization of the matrix monomer or prepolymer. Interconnectedness of the oxide network can have a strong influence on mechanical, permeability and electrical conductivity of the material.

By appropriate matching of the surface properties of the nanoparticles and the matrix monomer it is possible to make a one phase system or generate a very fine phase separation that is insufficient to scatter light. This is of specific importance in many applications since the ability to uniformly photocure several millimeter thicknesses of material to a solid is rendered. In addition, opacifying particles can be added to the transparent base for better control of cosmetic features.

The invention will be further described in connection with the following examples which are set forth for purposes of illustration only.

EXAMPLE 1

Tantalum Oxide Nanoparticle Synthesis (a). Chlorotrimethylsilane (4.0019 g, 0.0368 mol), tantalum ethoxide (30,4454 g, 0.0749 mole), a-bis(trimethylsilyl) vinylphosphonate (3.9994 g, 0.0158 mol) and formic acid (7.1262 gm 0.1548 mol) were added in the above sequence under nitrogen while stiring at room temperature for 7 hrs (did not gel) before pumped vacuum for 20.5 hrs to give a white powder. The powder dissolved in methanol in two hours at 10 wt % concentration, the pH of the solution was about 2.

(b). Chlorotrimethylsilane (7.15 g. 0.0658 mol), tantalum ethoxide (56.09 g, 0.138 mole), 2-bis(trimethylsilyl) phosphonoethyl methacrylate (8.56 g, 0.0253 mol) and formic acid (13.16 g, 0.286 mol) were added in the written sequence under nitrogen with stirring 30° C. bath for 7.5 hr (it gelled at about 6 hrs). After vacuum pumping for 29 hrs, white powder was obtained. The powder dissolved in methanol in about two hours at 10 wt % concentration; the pH of the solution was about 2.

(c). Tantalum ethoxide (0.9707 g, 0.00239 mol), chlorovinyldimethylsilane (0.1194 g, 0.000990 mol), 3-(trimethylsily)propyl methacrylate (0.2056 g, 0.000828 mol) and formic acid (0.2026 g, 0.00440 mol) were added in the written sequence under nitrogen while being stirred. The resulting clear liquid turned viscous and eventually gelled in about 0.5 hr. The reaction mixture was left at room temperature for 17.5 hrs before being vacuum pumped for 8 hrs to give a white powder. The product dissolved in methanol at room temperature in one hour at 10 wt % concentration; the pH of the solution was about 3 to 4.

EXAMPLE 2

Tantalum Oxide Nanoparticle-isotropic Hydrophobic Monomer Glasses (a). 1.0187 g of the tantalum oxide methanol solution [9.5 wt %, neutralized with poly(4-vinylpyridine)] and 0.1970 g 2-hydroxylethylmethacrylate (HEMA) were mixed; the resulting clear solution was pumped under high vacuum. After complete evaporation of methanol and a small amount of HEMA, a clear liquid was obtained which contained 35 wt % tantalum oxide. The liquid gelled in 30 mins.

(b)(i). 1.2901 g of the tantalum oxide methanol solution [10.1 wt %; neutralized with poly(4-vinylpyridine)] and 0.4033 g HEMA were mixed; the resulting clear solution pumped under high vacuum. After complete evaporation of methanol and a small amount of HEMA, a clear liquid was obtained which contained 29.6 wt % tantalum oxide. The liquid gelled days later.

(ii). 6.2518 g of the tantalum oxide methanol solution [8.7 wt %; neutralized with poly94-vinylpyridine)], 1.2835 g glycerol dimethacrylate and 0.0073 g camphorquinone were mixed; the resulting clear yellow solution was pumped under high vacuum. After the complete evaporation of methanol, a clear yellow liquid resulted; after addition of 0.0078 g dimethylaminoethyl methacrylate, the liquid was photocured for 3 mins each side and transparent, slightly yellow composite was obtained. This composite contains 29.6 wt % of tantalum oxide. The point bending specimen showed solvent stress crasing after prolonged exposure to saline solution at 37° C.

(iii). In the following examples, neutralized tantalum oxide methanol solution was first reacted with a silane compount [vinylethoxydimethylsilane, chlorovinyldimethylsilane, ethoxytrimethylsilane or 3-(trimethoxysily)propyl methacrylate] at elevated temperature before the addition of monomers. The resulting clear solutions were vacuum pumped as detailed in the following table.

| No | Reagent | Reaction time (hr) and temperature (° C.) | Composition and results |
|---|---|---|---|
| 1 | Ta$_2$O$_5$/CH$_3$OH (9.97%) 1.5085 g ethoxytrimethylsilane 0.5 mL | 1.5 hr; 55–56 | Ta$_2$O$_5$ 0.1504 g (22.9%) PPGMMA 0.5065 g (77.1%) clear liquid for at least 26 hrs at RT |
| 2 | Ta$_2$O$_5$/CH$_3$OH (9.97%) 1.6450 g ethoxytrimethylsilane 0.6 mL | 2.0 hr; 53 | Ta$_2$O$_5$ 0.1640 g (29.6%) PPGMMA 0.3898 g (70.4%) clear liquid for at least 1.8 hrs at RT |

-continued

| No | Reagent | Reaction time (hr) and temperature (° C.) | Composition and results |
|---|---|---|---|
| 3 | Ta$_2$O$_5$/CH$_3$OH (9.97%) 1.5 mL ethoxytrimethylsilane 0.5 mL | 5.4 hr; 53 | Ta$_2$O$_5$ 0.12 g (19%) PPGMMA 0.3536 g (55.6%) unity cement 0.1621 g (25.4%) small amount of liquid spread on wall of RBF (gelled at bottom) which gelled within 16.8 hr |
| 4 | Ta$_2$O$_5$/CH$_3$OH (10.89%) 8.1764 g ethoxytrimethylsilane 10.0 mL | 48 hr; 52 | (A)Ta$_2$O$_5$ 0.4473 g (30.1%) unity cement 1.0372 g (69.9%) very viscous clear liquid which gelled within 3.5 hr at RT; photocured 60s to a hard, transparent specimen (B)Ta$_2$O$_5$ 0.4253 g (29.9%) UDMA 0.9985 g (70.1%) clear sticky gel resulted; photocured 60s to a hard, slightly hazy specimen |
| 5 | Ta$_2$O$_5$/CH$_3$OH (10.89%) 1.6724 g vinylethoxytdimethyl-silane 0.6 mL | 3.3 hr; 55–58 | Ta$_2$O$_5$ 0.0578 g (26.3%) PPGMMA 0.1622 g (73.7%) clear liquid for at least 17.2 hr stored at RT |
| 6 | Ta$_2$O$_5$/CH$_3$OH (10.89%) 1.7900 g TMSPMA 0.5 mL | 4.4 hr; 50–55 | Ta$_2$O$_5$ 0.1949 g (16.3%) TMSPMA 0.52 g (43.3%) PPGMMA 0.4836 g (40.4%) clear liquid for more than a month at RT |
| 7 | Ta$_2$O$_5$/CH$_3$OH (10.89%) 4.5434 g TMSPMA 0.5 mL | 26.3 hr; 51–53 | Ta$_2$O$_5$ 0.4689 g (30.1%) TMSPMA 0.4589 g (29.4%) unity cement 0.6311 g (40.5%) viscous clear liquid for at least 1 hr at RT; photocured 60s to a hard, transparent specimen (w/bubbles) |
| 8 | Ta$_2$O$_5$/CH$_3$OH (10.89%) 1.0603 g chlorovinyldimethyl-silane 1.0 mL | 15.8; 53 | Ta$_2$O$_5$ 0.1155 g (28.2%) unity cement 0.2940 g (71.8%) yellow liquid for at least 30 hr at RT; photocured 120s to a hard, transparent specimen |

PPGMMA --- polypropylene glycol monomethacrylate (Polysciences, Mw 360–390)
RBF --- round bottom flask (c) The above reaction was scaled up to three times and used to prepare samples from three point bending tests as detailed in the following. 1.4341 g of the tantalum oxide powder was dissolved in 11.08 g methanol followed by neutralization with 0.2246 g lightly crosslinked poly94-vinylpyridine). After centrifuging to remove the poly94-vinylpyridine), the supernatant methanol solution of tantalum oxide with a pH of about 6 was then reacted with 4.5 mL vinylethoxydimethylsilane at about 50° C. for 24 hours before the addition of 3.01 g matrix monomer resin followed by evaporation of solvent and excess vinylethoxydimethylsilane under high vacuum. The matrix monomer utilized was the hydrophobic, photopolymerizable Unity cement (Coltene).

A clear yellow free flowing liquid resulted when all the solvent was removed. The liquid was put into transparent silicone, three point bending molds and photocured with blue light from a dental curing lamp for 60s from both top and bottom side to give transparent, slightly yellow samples. The final composition was 30 wt % tantalum oxide nanoparticles and 70% matrix monomer.

The three point bending fracture strength of nanoparticle composite was compared with Unity cement and a Unity cement containing 70 wt % microfiller is compared in FIG. 1 after soaking for 24 hrs in saline solution at 37° C.; none of the samples showed any evidence of stress crazing. Although the transparent nanoparticle composite is weaker than the opaque microfilled Unity cement and the unfilled unity cement, it has the advantages of optical transparency, more univorm photocure, and radioopacity.

The three point bending results are shown in the following tables:

| Material | Flexural Strength |
|---|---|
| Pure UC | 15,271.66 |
| Filled UC | 18,658.58 |
| Ta2O5 | 7,482.17 |

| | Pure UC | Filled UC |
|---|---|---|
| t-Test: Two-Sample Assuming Unequal Variances | | |
| Mean | 15271.656 | 18658.58225 |
| Variance | 2876336.2 | 4778286.125 |
| Observations | 9 | 11 |
| Hypothesized Mean Difference | 0 | |
| df | 18 | |
| t Stat | −3.900544 | |
| P(T <= t) one-tail | 0.0005241 | |
| t Critical one-tail | 1.7340631 | |
| P(T <= t) two-tail | 0.0010481 | |
| t Critical two-tail | 2.1009237 | |

| | Pure UC | Ta2O5 |
|---|---|---|
| t-Test: Two-Sample Assuming Unequal Variances | | |
| Mean | 15271.656 | 7482.166873 |
| Variance | 2876336.2 | 1411017.661 |
| Observations | 9 | 13 |
| Hypothesized Mean Difference | 0 | |
| df | 13 | |
| t Stat | 11.904735 | |
| P(T <= t) one-tail | 1.15E-08 | |
| t Critical one-tail | 1.7709317 | |
| P(T <= t) two-tail | 2.299E-08 | |
| t Critical two-tail | 2.1603682 | |

EXAMPLE 3

Synthesis and Purification of Liquid Crystal Monomers

A. The initial step comprises reacting the compounts set forth in the table below.

| Compound | Ethyl-4-Hydroxy-Benzoate | Potassium Hydroxide | 6-Chloro-1-Hexanol | Sodium Iodide | C6 |
|---|---|---|---|---|---|
| Equivalents | 1 | 1.2 | 1.2 | 1.4 | 1 |
| Formula Weight | 166.177 | 56.11 | 136.62 | 149.89 | 238.28 |
| Millimoles | 609.96 | 731.96 | 731.96 | 853.94 | 609.93 |
| Mass | 101.36 | 41.07 | 100 | 127.99 | 145.33 |

The reaction is as follows:

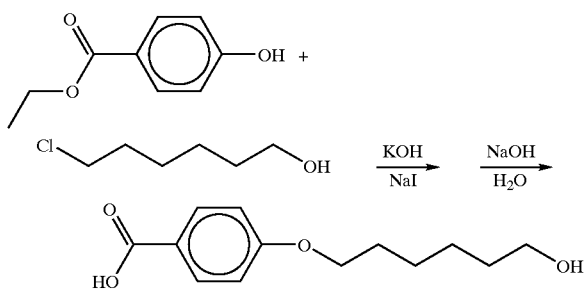

A flame dried 2 liter, three neck round bottom flask was outfitted with a water cooled condenser and stir bar and cooled under house nitrogen. To this was added 101.36 grams (610.0 mmol) of ethyl4-hydroxy benzoate (99%, Acros 15025-0010), 500 milliliters of acetone (Fisher Optima, used as received only from a fresh bottle) and 41.07 (732.0 mmol) of potassium hydroxide (ACS Certified, Fisher Scientific P250-500). This was stirred until the potassium hydroxide dissolved entirely, producing a small amount of clear oil on the walls of the flask. The reaction was mildly exothermic, the flask becoming warm to the touch as the KOH dissolved. Heat may help speed the dissolution of the KOH, but this was not necessary. At room temperature, 100 grams (732 mmol) of 6-chloro-1-hexanol (95%, Acros10928-1000) and 128 grams (854 mmol) of sodium iodide (Anhydrous, 99+%, Acros 20318-0010) were added to produce a clear solution with a dispersed white solid. The white solid can interfere with the stir bar, and unless a really good stir plate and stir bar were used, mechanical stirring was needed. An additional 500 ml of acetone was added. The acetone was added in two aliquots because it comes in 500 ml bottles and thus the walls of the flask and the funnels can be rinsed down with each addition of reagents. This is heated to reflux for 24 to 48 hours. As the reaction reaches completion, a large amount of waxy tan precipitate lines the walls of the flask. The best test for completion, however, is to monitor the reaction by TLC for significant disappearance of the starting materials.

A convenient spot test for 6-chloro-1-hexanol, which does not show up by fluorescence or iodine, is to immerse the TLC plate in a solution containing 4 ml of concentrated sulfuric acid in 100 ml of methanol. The TLC plate is heated to 200° C. on a glass plate and a charred brown spot appears. Only the product and 6-chloro-1-hexanol are charred with sulfuric acid.

TLC of the reaction mixture in ether on a silica gel plate shows UV active spots at RF=0.72, 0.62, 0.45, 0.29, 0.18, and 0.00 and spots that were charred with sulfuric acid at RF=0.53 and 0.45. The largest spot, which corresponds to the ethanol ester of the product appears at RF=0.45 and is observable with UV and the sulfuric acid stain. The product spot overlaps the acid charred spot at RF=0.53 which corresponds to 6-chloro-1-hexanol. However, they remained distinct, even when additional 6-chloro-1-hexanol is spotted with the product. A small amount of 6-chloro-1-hexanol and ethyl-4-hydroxy benzoate (RF=0.62) are evident in the reaction mixture.

After significant disappearance of the starting material was observed, the solution was filtered by gravity. The filtrate and the waxy precipitate lining the flask walls were dissolved in water and a small amount of ether. It appeared to be a salt dispersed in insoluble organic material, as it did not dissolve fully until the ether was added. The supernatant acetone was removed in vacuo at 60° C. and the residue was dissolved in ether and a small amount of water. The two were then recombined in a separatory funnel and the aqueous phase extracted three times with ether. This process of separating and recombining the solid and liquid phases of the reaction ensures all solids are fully dissolved and helps avoid serious emulsions during the extraction.

Ether was removed in vacuo, and the residue was refluxed with an aqueous solution containing 34 grams of sodium hydroxide (855 mmol) for 4 to 12 hours. Typically, the solution was diluted with water to make a total volume of 500 to 800 ml. This produced a yellow solution containing the sodium salt of our product, along with residual starting materials. The aqueous solution of the sodium salt is only meta-stable, and the salt can precipitate if cooled in ice or allowed to stand for a few hours at room temperature. Addition of more water (possibly diluting up to 3 liters) along with slight warming can help redissolve the precipitate.

The solution was extracted three times with ether to remove residual starting material. The aqueous phase was then titrated to a pH of 3 with 6N HCl, forming a white precipitate. The mixture is filtered and the solid recrystallized from isopropanol and washed with hexanes.

On one occasion, I forgot the second extraction and titrated the aqueous solution directly after the saponification reaction. There was still a lot of 6chloro-1-hexanol present (identified by smell) after the first recrystallization, but a second recrystallization from IPA removed it entirely (verified by NMR and melting point). This could possibly be the best method, because the product can be precipitated from the hot aqueous solution, well before crystals of the sodium salt have a chance to grow. I have duplicated this method, and the yield is comparable to that when the saponified product is extracted with ether.

At times it has been difficult to recrystallize the product, especially if the sodium salt has precipitated from solution. Not all of the material would dissolve in boiling IPA, and hot filtration seemed to have no effect. Some powder was retained on the paper, but crystals that formed in the receiving flask as the filtrate cooled were even more difficult to dissolve. It is possible that small amounts of the sodium salt are responsible. This problem has appeared intermittently, both when the saponified product was extracted with ether, and the ether extraction step was skipped.

The reaction yields ranged from 100–114 grams (68–78%)

B. Second Step-Acryloylation

| Compound | C6 | DMA | Acryloyl Chloride | C6-Acr |
|---|---|---|---|---|
| Equivalents | 1 | 1.3 | 1.15 | 1 |
| Formula Weight | 238.28 | 121.18 | 90.51 | 329.02 |
| Millimoles | 329.02 | 427.7 | 378.4 | 329.02 |
| Mass (g) | 78.4 | 51.83 | 34.25 | 96.18 |

The reaction is as follows:

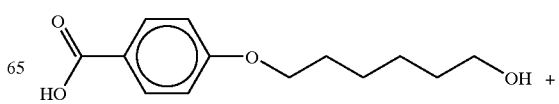

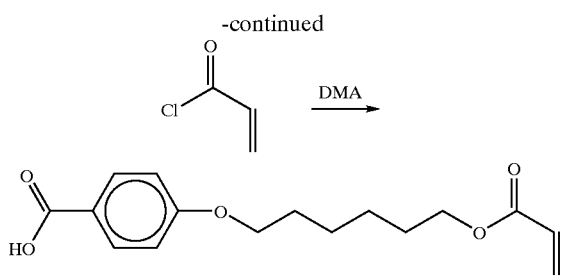

This is a troublesome reaction, in which a hydrochlorinated impurity appears. The general reaction scheme involves the reaction of C6 with acryloyl chloride in the presence of a base or catalyst.

In a generalized procedure, 31.4 grams of C-6 (132 mmol) was dissolved in 500 ml THF at 60 EC. Dimethyl aniline (171 mmol) was added by pipette. Freshly distilled acryloyl-chloride was added by pipette (150 mmol) drop-wise. This produced a white precipitate and caused a somewhat vigorous exothermic reaction. The solution was stirred for 24–48 hours until substantial amount of the starting material has disappeared as evident by TLC in ether. The starting material has a UV fluorescence inhibiting spot at RF=0.26. The product has a UV fluorescence inhibiting spot at RF=0.50. There are other less significant fluorescence inhibiting spots of unknown origin (suspected acryloyl anhydride of product and starting material respectively) at RF=0.56 and RF=0.33.

After the reaction is finished, THF was removed in vacuo and the residue was partitioned between methylene chloride and water. The organic phase was extracted three times with water (very gently to avoid emulsion) and each time the aqueous pH is reduced to 3 to help remove amines. The organic phase was collected, dried in vacuo, and the residue recrystallized from isopropanol. (Yield=85–90%).

There are two coupled triplets in the proton NMR spectrum at 2.9 and 3.9 ppm. These are most likely the product of HCl addition across the double bond, forming a 3-chloropropionate. NMR simulations corroborate this hypothesis. Relative concentrations of the 3-chloro-propionate impurity were estimated by comparing the integration value of the impurity peaks with the value of the allyl protons in the spectrum. The product contains approximately 8 to 10% impurity when synthesized in THF. Amounts can range from 0–4% when synthesized in chloroform to 20–25% when synthesized in THF without a base. Our preferred method is to use chloroform as a solvent although the yield is low (48%).

Variations include:

Chloroform

Our C-6 starting material was barely soluble. C6, Dimethylaniline, and acryloyl chloride were added to chloroform (Fisher Optima, used as received and stored under nitrogen) at room temperature and heated to reflux. (10 ml of chloroform for each 1 g of starting material C6) After 12 hours, most of the powder has dissolved, forming a slightly cloudy solution. The starting material was mostly gone by TLC. After recrystallization, NMR shows that the chloropropionate impurity has been reduced to 0–4%.

Pyridine

The use of pyridine as the base or a combination of pyridine and dimethylaminopyridine catalyst has produced a low yield in every instance. The impurity is still present when pyridine and THF are used together. The reaction of acryloyl chloride is more vigorous than with dimethylaniline and caution should be used when it is added. Addition of 15% excess acryloyl chloride produced an incomplete reaction as observed by TLC. Addition of 100% excess acryloyl chloride removes the starting material, but isolated yields are still low. This is true for using pyridine in a variety of solvents and using pyridine as the solvent.

Dioxane

Our C-6 starting material was added to dioxane (10 ml for every gram) and heated to 60 EC to produce an inhomogenous mixture. Dimethyl aniline was added. Acryloyl chloride was added dropwise (nothing exciting happens, but the solution clears). Reaction products include our the 3-chloropropionate impurity, and an additional impurity with similar NMR shifts.

The best way to work the reaction up is to add one aliquot of both methylene chloride and water (i.e. 50 ml of DCM and 50 ml of water to 50 ml of dioxane) to the reaction solvent, and to extract the organic phase three times with water, removing most of the dioxane as well as any amines.

| Compound | C6-Acr | t-butyl-hydro-quinone | TEA | MeSO2Cl | DMAP |
|---|---|---|---|---|---|
| Equivalents | 2 | 1 | 4.2 | 2.1 | 0.2 |
| Formula Weight | 292.33 | 166.22 | 101.19 | 114.55 | 122.17 |
| Density | | | 0.726 | 1.48 | |
| Millimoles | 269.5 | 134.8 | 566 | 283 | 26.95 |
| Amount | 78.8 g | 22.4 g | 78.9 ml | 21.9 ml | 3.29 g |

The reaction is as follows:

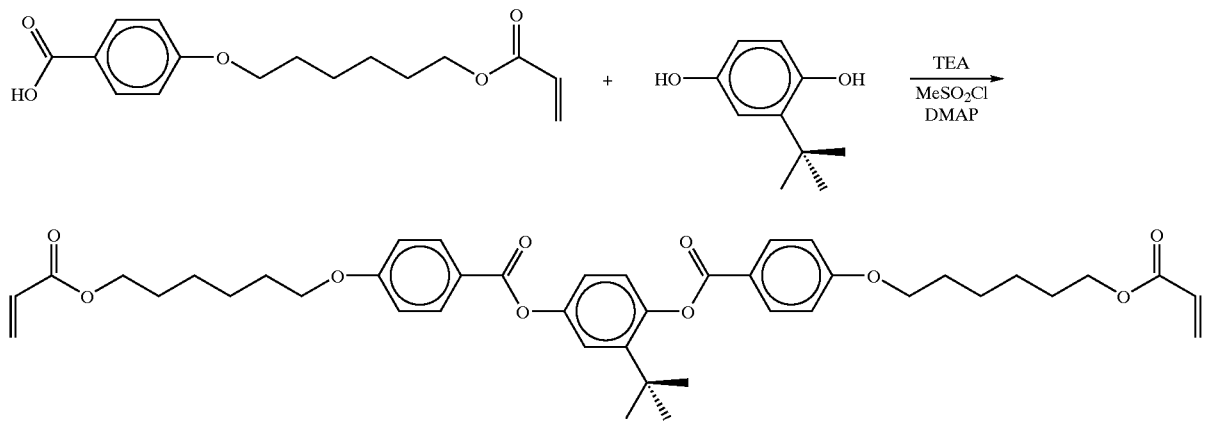

C6-Acr was dissolved in freshly distilled, anhydrous THF (20 ml/gram) and cooled in a dry ice/acetone bath, forming a clear yellow solution. TEA and Methane-sulfonyl-chloride were added, forming a cloudy yellow solution. This was allowed to stir for 1 hour, and t-butylhydroquinone and dimethylaminopyridine were added. This was warmed to 0° C. and stirred overnight, warming to room temperature as the ice in the cooling bath melts. The white precipitate was filtered by gravity, and the resultant yellow solution partitioned between methylene chloride and water. The aqueous phase was titrated to pH=2 (measured after stirring) and the organic phase was collected and extracted two more times with water. Sometimes it was necessary to add a half saturated NaCl solution to avoid emulsions. It is helpful to stir the extractions gently, as opposed to shaking to avoid emulsions.

Chloroform was removed in vacuo, and the resultant paste is purified by either liquid chromatography or recrystallization.

Yield is about 70 ml of crude product, but only a few grams after purification.

D. Liquid Chromatography

Samples of the C6-LX were purified by liquid chromatography over silica gel using 1:1 (v:v) solution of hexanes and ethyl ether. The silica gel purchased from Aldrich (stock number 28,859-4) was 200–400 mesh, 60 angstrom with a BET surface area of 500 $m^2/g$ and a pore volume of 0.75 $cm^3/g$. The size of the silica column was 50 mm diameter by 33 cm length. Ether was added to our sample until it could be transferred by pipette, and it was added to the column to produce a 2 mm tall band (about 4 ml). Three 100 ml fractions were collected, followed by 9 ml fractions. Pure C6-LX eluted between about 950 ml and 1400 ml of solvent eluted (including the fore-fractions). The solvent was removed in vacuo and the resulting oil recrystallized by dissolving in about 3 ml of ether and placing in the freezer (−10 EC). About 500 mg of pure compound was isolated for each column run. There is a substantial amount of material at the top of the column (RF=0) which appears to be polymerized product. This indicates that further precautions should be taken to prevent polymerization. The procedure yields about 15% pure C6-LX, compared to the amount of crude material loaded on the column.

E. Recrystallizing C10-LX

After the coupling reaction, 25 ml of crude material was dissolved in methylene chloride and gently extracted (no shaking to avoid emulsion) three times with dilute HCl (pH=4). The methylene chloride was removed in vacuo at 30 degrees and the sample was washed into boiling methanol to produce a cloudy liquid. As the mixture cooled to room temperature, a brown oil collected on the bottom of the flask. The mixture was wrapped in aluminum foil and allowed to sit for three days at room temperature. It was then moved to the refrigerator at about 5 degrees where is sat for another two days. Finally, it was moved into the freezer at about −10 degrees, and a yellowish white solid formed in the bottom of the flask. TLC shows the solid is remarkably enriched with the top 2 TLC spots, whereas the liquid contained almost entirely the lower spots of the crude reaction mixture. After melting, the solid was liquid crystalline at room temperature.

The solid was again washed with hot methanol and placed in the refrigerator. After 3 days, several small white crystals formed on the walls of the flask. The crystals continued to grow for about two days, after which the brown oil precipitated as a yellowish white solid. The white crystals from the walls of the flask had a melting point of 37–38 EC. The yellowish solid from the bottom melted to a liquid crystal at room temperature. TLC showed only the top spot (RF=0.34), and NMR showed no difference in purity between the two. The chloropropionate impurity, which is evident only by NMR, was present in the same concentration in both samples.

In an attempt to remove the impurity, a small sample of the white crystals was dissolved in ether, and a portion was passed through a silica gel pipet column. A second portion was passed through a column of Aldrich Acidic Alumina. NMR showed a slight decrease in the impurity concentration (maybe as much as 10%), but no strong cleaning effect.

After decanting the methanol, the white crystals and brownish liquid crystal were allowed to sit at room temperature in the dark of one week. TLC revealed additional spots, in smaller concentrations at RF=0.30 and RF=0.24. Furthermore, a weakly UV active streak continued from the lowest spot to the baseline. These seem to indicate slow polymerization of the material.

EXAMPLE 4

Tantalum Oxide Nanoparticle-liquid Crystal Monomer Composites (1) Recrystalized liquid crystal monomer (C6) 0.0062 g in 0.42 g ethyl ether and 8.5 wt % tantalum oxide methanol solution [(from example 1, No. 3) were mixed to a slightly couldy solution and neutralized with poly(4-vinylpyridine)]. The solution was deposited onto a microscope slide and after the evaporation of solvent a white opaque paste resulted. (The composite contained 30.5 wt % tantalum oxide). Optical microscopy under crossed polarizers revealed that some crystallization ($T_m$=60° C.) had occurred; however, when, the sample was melted and cooled a reversible $T_{n->i}$ phase transition was seen at ca. 40° C. The sample did not crystallize upon standing at room temperature.

(2). Crude liquid crystal monomer C6(H,TB,H), 15% hydrochlorination impurity) 0.0342 g in 0.37 g 2-methoxy ethyl ether and 8.5 wt % tantalum oxide methanol solution [(from example 1, No. 3) were mixed to a clear solution and neutralized with poly(4-vinylpyridine)] were mixed to a clear solution. The solution was deposited onto a microscope slide and pumped dry under high vacuum. A translucent white paste was obtained after the evaporation of solvent. (The resulting composite contained 30.9 wt % tantalum oxide). Optical microscopy under crossed polarizers revealed that some crystallization ($T_m$=60° C.) had occurred; however, when, the sample was melted and cooled a reversible $T_{n->i}$ phase transition was seen at ca. 40° C. The sample did not crystallize upon standing at room temperature.

(3) Crude liquid crystal monomer, C6(H,TB,H), 15% hydrochlorination impurity), 0.1982 g dissolved in 1.75 g ethyl ether was added slowly to 1.0040 g 8.5 wt % tantalum oxide mthanol solution [(from example 1, No. 3); neutralized with poly(4vinylpyridine)] with 0.0011 g camphorquinone and 0.0011 g ethyl-4-dimethylaminobenzoate. The resulting solution was slightly cloudy. The solution was deposited in a mold and the solvent evaporated under vacuum. A sticky, yellow paste was formed with was photocured with a blue light dental curing lamp for 60s to give a hard, light yellow opaque specimen (The composite contained 30.2% tantalum oxide).

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Nanoparticles comprising an amphoteric metal oxide comprising a metal atom which is complexed with first and second oxygen atoms which are bound to the same phosphorous atom in a phosphonate group, said amphoteric metal oxide also comprising a third oxygen atom bound to a silicon atom of a silyl group.

2. The nanoparticles of claim 1 wherein said metal oxide is tantalum oxide.

3. The nanoparticles of claim 1 wherein said silyl group is a vinyl dimethyl silyl group.

4. The nanoparticles of claim 2 wherein said silyl group is a vinyl dimethyl silyl group.

5. The nanoparticles of claim 1 wherein said phosphorous also is bound to a photopolymerizable group selected from the group consisting of a vinyl group, an acryloyl oxyethyl group, and a methacryloyl oxyethyl group.

6. The nanoparticles of claim 2 wherein said phosphorous also is bound to a photopolymerizable group selected from the group consisting of a vinyl group, an acryloyl oxyethyl group, and a methacryloyl oxyethyl group.

7. The nanoparticles of claim 3 wherein said phosphorous also is bound to a photopolymerizable group selected from the group consisting of a vinyl group, an acryloyl oxyethyl group, and a methacryloyl oxyethyl group.

8. The nanoparticles of claim 4 wherein said phosphorous also is bound to a photopolymerizable group consisting of a vinyl group, an acryloyl oxyethyl group, and a methacryloyl oxyethyl group.

9. The nanoparticles of claim 5 wherein said photopolymerizable group is bound to a liquid crystal monomer which is photopolymerizable at room temperature.

10. Nanoparticles comprising an amphoteric metal oxide comprising a metal atom which is complexed with first and second oxygen atoms which are bound to a phosphorous atom in a phosphonate group, said amphoteric metal oxide also comprising a third oxygen atom bound to a silicon atom of a silyl group; wherein said phosphorous atom also is bound to a photopolymerizable group selected from the group consisting of a vinyl group, an acryloyl oxyethyl group, and a methacryloyl oxyethyl group, said photopolymerizable group being bound to a liquid crystal monomer comprising bis(4-(6-acryloyloxy-A-1-oxy)benzoyl)2-(t-butyl)quinone in which A is selected from the group consisting of a hexyl group, a heptyl group, an octyl group, a nonyl group, a decyl group, or a mixture of such monomers.

11. Nanoparticles comprising an amphoteric metal oxide comprising a metal atom which is complexed with first and second oxygen atoms which are bound to a phosphorous atom in a phosphonate group, said amphoteric metal oxide also comprising a third oxygen atom bound to a silicon atom of a silyl group, said phosphorous atom also being bound to a photopolymerizable group selected from the group consisting of a vinyl group, an acryloyl oxyethyl group, and a methacryloyl oxyethyl group, said photopolymerizable group being bound to liquid crystal monomers comprising bis(4-(6-acryloyloxy-A-1-oxy)benzoyl)2-(t-butyl)quinone in which A is selected from the group consisting of a hexyl group, a heptyl group, an octyl group, a nonyl group, a decyl group, or a mixture of such monomers, said liquid crystal monomers comprising acryloyloxy groups at each end comprising a terminal carbon-carbon double bond, wherein at least one of said terminal carbon-carbon double bonds is reacted with an impurity such as hydrochloric acid.

12. Nanoparticles comprising amphoteric metal oxide comprising metal atoms complexed with first and second oxygen atoms bound to the same phosphorous atom in a phosphonate group, said amphoteric metal oxide also comprising a third oxygen atom bound to a silicon atom of a silyl group, said phosphorous atom also being bound to a photopolymerizable group bound to a liquid crystal monomer which is photopolymerizable at room temperature.

13. The nanoparticles of claim 12 wherein said liquid crystal monomer is a bis(4-(6-acryloyloxy-A-1-oxy)benzoyl)2-(t-butyl)quinone wherein A is selected from the group consisting of a hexyl group; a heptyl group, an octyl group, a nonyl group, a decyl group, or a mixture of such monomers.

14. The nanoparticles of claim 13 wherein said monomers comprise first and second ends comprising acryloyloxy groups comprising terminal carbon-carbon double bonds, wherein at least one of said terminal carbon-carbon double bonds is reacted with an impurity such as hydrochloric acid.

15. Nanoparticles comprising amphoteric metal oxide comprising tin complexed with first and second oxygen atoms bound to the same phosphorous atom in a phosphonate group, said amphoteric metal oxide also comprising a third oxygen atom bound to a silicon atom of a silyl group.

16. The nanoparticles of claim 15 wherein said silyl group is a vinyl dimethyl silyl group.

17. The nanoparticles of claim 15 wherein said phosphorous also is bound to a photopolymerizable group selected from the group consisting of a vinyl group, an acryloyl oxyethyl group, and a methacryloyl oxyethyl group.

18. The nanoparticles of claim 16 wherein said phosphorous also is bound to a photopolymerizable group selected from the group consisting of a vinyl group, an acryloyl oxyethyl group, and a methacryloyl oxyethyl group.

19. The nanoparticles of claim 17 wherein said photopolymerizable group is bound to a liquid crystal monomer which is photopolymerizable at room temperature.

20. The nanoparticles of claim 19 wherein said liquid crystal monomer is a bis(4-(6-acryloyloxy-A-1-oxy)benzoyl)2-(t-butyl)quinone in which A is selected from the group consisting of a hexyl group, a heptyl group, an octyl group, a nonyl group, a decyl group, or a mixture of such monomers.

21. The nanoparticles of claim 20 wherein said monomers comprise first and second ends comprising acryloyloxy groups comprising terminal carbon-carbon double bonds, wherein at least one of said terminal carbon-carbon double bonds is reacted with an impurity such as hydrochloric acid.

* * * * *